(12) United States Patent
Russo et al.

(10) Patent No.: US 6,462,088 B1
(45) Date of Patent: Oct. 8, 2002

(54) DISINFECTING PREPARATION CONTAINING CHLORINE IN ALCOHOL

(75) Inventors: Antonello Russo, Trieste; Hana Dannan, Ivrea, both of (IT)

(73) Assignee: Eurospital S.p.A., Trieste (IT)

( * ) Notice: Subject to any disclaimer, the term of this patent is extended or adjusted under 35 U.S.C. 154(b) by 0 days.

(21) Appl. No.: 09/735,916

(22) Filed: Dec. 14, 2000

(30) Foreign Application Priority Data

Jun. 15, 1998 (IT) .................................... RM98A000389

(51) Int. Cl.⁷ .................. A01N 41/06; A01N 31/02; A01N 25/02; A01N 25/22; A61L 2/18
(52) U.S. Cl. .................. 514/604; 514/612; 514/724; 514/739; 514/970; 422/29; 422/37
(58) Field of Search ................................ 514/604, 612, 514/724, 739, 970; 422/29, 37

(56) References Cited

FOREIGN PATENT DOCUMENTS

RO         114628        * 6/1999

OTHER PUBLICATIONS

Chemical Abstracts 134: 239350, Abstracting RO114,628, 1999.*

The Merck Index, 12th ed., Merck & Co., Whitehouse Station, NJ, p. 1473, item 8739, 1996.*

* cited by examiner

*Primary Examiner*—John Pak
(74) *Attorney, Agent, or Firm*—Nixon & Vanderhye P.C.

(57) ABSTRACT

Liquid germicidal formulation containing, as the active ingredients, a combination of an alcohol and an organic N-chloroamine, which combination shows a high bactericidal activity and an unexpected stability in time, while maintaining its effectiveness substantially unchanged even after a prolonged storage. The formulation comprises, in water, chloramine-T or chloramine-B and one or more, aliphatic alcohols having up to 12 carbon atoms, preferably isopropanol, said solution having a pH not lower than 8.5.

10 Claims, No Drawings

DISINFECTING PREPARATION CONTAINING CHLORINE IN ALCOHOL

SPECIFICATION

The present invention concerns a disinfecting preparation containing chlorine in alcohol. More specifically, the invention relates to a liquid germicidal formulation containing, as the active ingredients, a combination of an alcohol and an organic N-chloroamine, which combination shows a high bactericidal activity and an unexpected stability in time, while maintaining its effectiveness substantially unchanged even after a prolonged storage.

The bactericidal properties of alcohols, known since ancient times, have been studied on a scientific basis starting from the beginning of this century. Some of such products, firstly ethyl alcohol and isopropyl alcohol, have reached in the field of disinfectants a quite remarkable diffusion, also in view of the advantages connected with their water solubility, with the ease of evaporation and with their reduced toxicity. Actually, some higher aliphatic alcohols are more effective than the lower ones as antimicrobial agents, the highest effectiveness being reached by alcohols having 6–8 carbon atoms. However, the low volatility and the unpleasant odor of these compounds have greatly limited their use. Also some aromatic alcohols find some limited application as disinfectants, among which benzyl alcohol and phenethyl alcohol. The latter, however, suffer from the disadvantage of being more toxic.

Ethanol shows its maximum potency as a 60–75% aqueous solution (weight percentage), while solutions of lower or even higher concentration take a longer time to exert the same germicidal effects. Both alcohols with three carbon atoms, i.e. n-propanol and isopropanol, show a higher activity than ethanol, with a maximum level at concentrations around 60% by weight. In spite of their unquestioned antibacterial activity, from the point of view of the activity spectrum aliphatic alcohols have the drawback of being totally ineffective against spore-forming micro-organisms.

Another product the use of which as disinfectant is well established since the last century is chlorine. Chlorine was employed, in the form of calcium chloride, for treating the sewage of the city of London in the mid-XIX century. In the same period, chlorine was used as a disinfectant in the hospital of Dr. Semmelweis in Vienna, to fight the puerperal fever. Although the mechanism of action of chlorine has not yet been fully clarified, it is believed that chlorine performs its disinfecting action by releasing in water hypochloric acid (HClO), which is responsible for the destruction of micro-organisms. The concentrations of active chlorine required to kill most of the bacterial species may be of the order of 1 ppm, while higher concentrations are normally required to destroy spores and mycobacteria.

In the current practice, the term chlorine disinfectant is generically employed to refer to any disinfectant consisting in an aqueous solution of chlorine, hypochlorite or hypochlorous acid and also, in many cases, to other organic or inorganic chlorine-releasing compounds, such as, e.g., chloroamines ($ClNH_2$, $Cl_2NH$, $Cl_3N$), N-chlorosulfonamides (e.g., sodium N-chloro-p-toluenesulfonamide or chloramine-T, and sodium N-chlorobenzenesulfonamide or chloramine-B), N-chloroisocyanuric acids. Such compounds are also employed, at the same time, in view of their activity as chemical oxidants, and are consequently the most widely used products for the treatment of drinking water, for sanitizing swimming pools and for water treatment in the food industry.

In view of the foregoing, the interest in formulating a disinfectant containing, as the active ingredients, both alcohol and chlorine is quite clear. A similar preparation would join the antiseptic properties typical of each one of these two classes of compounds, thereby resulting in a product with an enhanced potency and a wider activity spectrum. Although the known art includes many disinfectants that combine the antibacterial activity of alcohols with the activity of other agents, such as, e.g., iodine, phenols or chlorhexidine, no preparations consisting of combinations of chlorine and alcohol appear to be presently on the market. This is apparently due to the strong oxidizing action exerted by chlorine on such organic products, that are known to be relatively easily oxidizable.

As it is known, the power of a compound as an oxidant is measured on one hand by thermodynamic factors, in particular by the standard oxidation potential of the compound, and on the other hand by kinetic factors, which govern the rate of the oxidation reaction. As a matter of fact, although in the absence of information on the reaction kinetics it is impossible to precisely foresee the performance of an oxidizing system, a first valuable indication is always found in the standard oxidation potentials. It is, actually, the high standard oxidation potential for the reduction of molecular chlorine to chloride ion ($Cl_2 + 2e^- \rightleftarrows 2Cl^-$) and that for the reduction of hypochloric acid to chloride ion ($HOCl + H^+ + 2e^- \rightleftarrows Cl^- + H_2O$)— respectively, $E_0 = 1.36$ V and $E_0 = 1.49$ V—that give the most immediate indication of the potency of the chlorine-based agents as chemical oxidants (see, e.g., R. G. Rice and M. Gomez-Taylor, Environmental Health Perspectives, 69, 31–44, (1986)).

In this connection, it has been shown experimentally (D. Coates and J. E. Death, Journal of Clinical Pathology, 31, 148–152, (1978)) that mixtures of various alcohols or glycols (i.e., methanol, n-propanol, isopropanol, ethanol and ethanediol) in aqueous solution at various concentrations (from 10 to 50% by weight) with sodium hypochlorite at a level of available chlorine of 2000 ppm, although having an interesting sporicidal activity when freshly prepared, had lost practically all available chlorine after few hours. In order to exploit the advantageous biological activity discovered, therefore, the concerned publication suggests to store the solutions of alcohol and hypochlorite in separate containers, and to mix them just before use.

A first measure aimed at limiting as much as possible the reactivity between alcohols and chlorine disinfectants may be to use, in a possible preparation, a chlorine source characterized by an oxidation potential lower than sodium hypochlorite, which is able to supply chlorine much more slowly than the common hypochlorites. Products particularly suitable to this end are the chloroamines, as it may be inferred from the following table. The table shows the standard oxidation potentials at 25° C. in aqueous solution (according to two different literature references, i.e. a): R. G. Rice and M. Gomez-Taylor, loc. cit.; b): Ullmann's Encyclopedia of Industrial Chemistry, 5th ed., VCH Verlagsellschaft A 28, 87 (1996)).

|  | $E_0$, V-Ref.[a] | $E_0$, V-Ref.[b] |
| --- | --- | --- |
| Chlorine | 1.36 | 1.36 |
| Hypochlorous acid | 1.49 | 1.50 |
| Hypochlorite ion | — | 0.90 |
| Chlorine dioxide | 1.275 | 1.71 |
| Monochloroamine | 1.16 | 0.75 |

Although they are not as powerful as chlorine, chloroamines have the advantage of being more stable, since they are less rapidly reactive. In water, chloroamines slowly hydrolyze, generating hypochloric acid according to the general reaction RR'NCl+H$_2$O ⇌ RR'NH+HOCl. In view of the fact that the bactericidal activity of these compounds is due to the release of hypochloric acid, the value of the equilibrium constant of the above reaction is used to express the activity of chloroamines as disinfectants. Since hypochloric acid is released gradually from these compounds, the latter may keep their disinfecting activity for longer periods of time, compared to hypochlorites.

Among the possible organic and inorganic compounds belonging to the family of chloroamines, the present invention is concerned with two specific agents, already mentioned in the foregoing, consisting in the monosodium salts of two N-chlorosulfonamides, i.e. N-chloro-p-toluenesulfonamide sodium salt or chloramine-T,

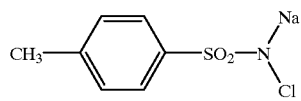

and N-chlorobenzenesulfonamide sodium salt or chloramine-B

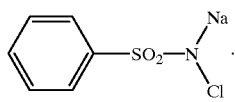

Both these compounds are known as topical antiseptics and for water sterilization, as they are active against a wide spectrum of microorganisms.

EP 372415 disclosed a process for the stabilisation of Chloramine-T and -B solutions according to which oxidation-resistant buffers (HEPPS and BICIN) are used at pH between 7 and 12.

U.S. Pat. No. 3,767,586 discloses a process for preparing stable solutions of N-halo compounds by reaction of a N-hydrogen compound, a halogen, an alkali or alkaline earth metal hydroxide, the presence of a buffer at pH 4.5–8.5.

Block, S. S., "Disinfection, Sterilisation and Preservation, Fourth Edition" (Pg. 143), Lea & Febiger, Philadelphia, US, describes inorganic chloramines and their use as bactericidal agents, including chloramine-T, whose bactericidal action is obtained at law pH and with long exposure.

As for all of the other chlorine disinfectants, the use of chloramine-T and chloramine-B in alcohol-based formulations was not considered to be commercially possible according to the current practice, in view of the oxidizing activity exerted by chlorine on alcohols.

One only known patent publication, i.e. patent No. 2255 of the former German Democratic Republic, issued in 1943, discloses antiseptic formulations which are said to contain both a chlorosulfonamide and aliphatic alcohols. However, such preparations also contain an organic dye extremely prone to oxidation, e.g. naphthol yellow S or 2,4,4-trinitrophenol sodium salt. According to the document, the alcohol prevents the organic dye from being oxidized by chloramine. From the comparative tests reported in the patent, a solution of naphthol yellow dye and chloramine-T in distilled water heated at 40° C. is rapidly degraded, as it is evidenced by the strong odor emanating from the solution, while a similar solution wherein 50% by volume of ethyl alcohol is present does not undergo any detectable odor changes. In the event that the temperature is kept at 50° C. for 16 hours, the concentration of active chlorine in the water solution of dye and chloramine-T is reduced by 92% by weight, while the concentration of active chlorine in the solution containing 50% of alcohol is reduced by 4.5% by weight only. Such a reduction is in any case too marked to allow to consider a disinfecting product stable according to the current standards. In addition, the document does not supply any specific indication that may be used to obtain, in general, alcohol solutions of chloramine-T or -B of any desired concentration, which are stable for quite long periods of time. On the contrary, the document seems to suggest that any formulation based on N-chlorosulfonamide and a dye, mixed with alcohols, may behave as a stable solution (within the limits inferrable from the example referred to above).

On the contrary, it has been found, according to the present invention, that a hydroalcoholic solution of chloramine-B or chloramine-T may remain stable for periods of time of several months, losing amounts of active chlorine of no more than few units per cent, provided that the pH of the solution is kept above 8.5, preferably above 9.5. The critical influence of pH may be explained if one considers that chloramines B and T, being strong electrolytes, readily dissociate in aqueous solution, thus transforming into the corresponding anionic form:

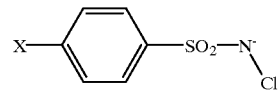

(wherein X may be a hydrogen atom or the —CH$_3$ group). In view of the markedly basic character of such species, it is expected that the attack by protons possibly present in the solution takes place quite easily through an acid-base equilibrium. Considering that the active species in the alcohol oxidation reaction is likely to be the protonated species, it may be understood that the pH can exert a great influence on the said reaction, hindering the reaction as much as the proton concentration is low.

In order to give an experimental confirmation of the above hypothesis, made in the frame of the invention, the following table shows the percent amount of available chlorine measured in aqueous solutions containing 60% by weight isopropanol and 10 g/l chloramine-B (equivalent to 2500 ppm of active chlorine), as well as various phosphate buffers, depending on the desired pH, the solution being kept at 40° C. for 4 weeks.

TABLE 1

Influence of pH on chlorine stability

| pH | % active chlorine after 4 weeks |
|---|---|
| 6.75–7.35 | 26 |
| 7.76–8.80 | 70 |
| 8.5–9.0 | 90 |
| 9.46–9.69 | 95 |
| 10.43–10.82 | 98 |

The data presented in the above table show that beyond a limit of pH close to 8.5 the stability of chlorine in time drastically increases. Above the concerned limit, the oxidation-reduction reaction of chloramine with alcohol appears to proceed extremely slowly, leaving practically unaltered the concentration of available chlorine.

Accordingly, the present invention specifically provides a disinfecting preparation containing chlorine in alcohol solution comprising, in water, chloramine-T or chloramine-B as defined above, and one or more aliphatic alcohols having up to 12 carbon atoms, said solution having a pH not lower than 8.5. Preferably, the said desired pH value is maintained in the disinfecting preparation by means of a suitable buffer.

In order to perform its germicidal activity at the level normally required to a disinfecting agent, the formulation according to the invention contains said chloramine-T or said chloramine-B at a concentration corresponding to 1000–2500 ppm of available chlorine, the optimal concentration being around 1100–1150 ppm of available chlorine. By way of example, a composition according to the invention containing 0.5% by weight of chloramine-T contains about 1120 ppm of active chlorine.

Preferably, the aliphatic alcohols are chosen from ethanol, n-propanol and isopropanol, and are present at a total concentration comprised between 40 and 70% by weight. It has been experimentally ascertained that the stability of chlorine in the solution according to the invention, measured by the percentage of available chlorine and referred to the starting concentration, after storage at a fixed temperature for a given period of time, is slightly higher for isopropanol solutions than for ethanol solutions. This finding, together with the already mentioned higher bactericidal activity of isopropyl alcohol compared with ethyl alcohol, makes isopropyl alcohol a preferred ingredient in the disinfecting formulations according to the invention.

In addition to possessing a high disinfecting power towards a wide spectrum of microorganisms and, moreover, a considerable sporicidal activity, the proposed preparation has also the property of removing any residues of adhesive tape. The latter is a quite important property in view of the use of the disinfecting product in out-patient treatment centers, in blood collection centers and in hospital departments, and cannot be obtained with alcohol-based disinfectants. Such property is a consequence, in the preferred embodiments of the invention, of the presence of a borate buffer in the composition. The borate buffer performs, on one hand, the function of maintaining the pH at the high levels desired (as the system $H_3BO_3/H_2BO_3^-$ has a pK of about 9.2 at 25° C., and thus has a buffering pH between 8 and 10) and, on the other hand, enhances the removal of any tape adhesive that may be present on the patient's skin. It is known, actually, that borate ion can remove the residues of the rubber adhesives currently used in adhesive medications and plasters.

The inclusion of the system boric acid/sodium hydroxide in the disinfecting formulation according to the invention also has the advantage of adding the two functions referred to above without interfering in any way with the system chloramine-alcohol, and without affecting the stability of such system. Comparative tests have evidenced that among the other possible agents able to give a good removal of the adhesive, such as, e.g., benzyl alcohol and dichloromethane, the borate buffer is able to assure the highest stability of chlorine. In addition, dichloromethane would bring about unacceptable toxicity problems for a disinfecting product for topical use as the one proposed herein.

The concentration range of the borate buffer that allows to obtain the maximum stability is quite limited, owing to the possibility of precipitation of sodium borate. Precipitation may occur, in particular, at low temperatures and in presence of an excess of sodium ions. Specifically, the optimal weight concentrations of the components of borate buffer in the formulation according to the invention are the following:

| | |
|---|---|
| boric acid | 0.153–0.155% |
| sodium hydroxide | 0.0396–0.064%. |

Thus, some particularly advantageous embodiments of the invention have the following parameters:

| | |
|---|---|
| chloramine-T or chloramine-B | 1000–2500 ppm of available chlorine |
| ethanol or isopropanol | 50–60% by weight |
| pH | >8.5. |
| boric acid | 0.153–0.155% by weight |
| sodium hydroxide | 0.0396–0.064% by weight |
| water | q.s. to 100%. |

Preferably, the chloramine is chloramine-T, at a concentration corresponding to 1100–1150 ppm of available chlorine, and the alcohol is isopropanol, at a concentration of 50% by weight. The pH of such preferred formulations is between 10.4 and 10.9. In order to achieve the maximum chlorine stability in the storage of the product for periods of time of at least several months, the preparation should be packaged in opaque containers, preferably dark, in order to avoid that the oxidation of alcohol is catalyzed by the electromagnetic radiation.

Some specific embodiments of the disinfectant formulation of the invention are described below for merely illustrative purposes, together with the results of the experimental studies carried out on the said formulation.

EXAMPLE

Production of a Disinfecting Preparation Containing Chlorine in Alcohol

The production of a preferred formulation according to the invention is carried out according to the following procedure, referred to a batch of 1000 kg of product:

1. 396 g of sodium hydroxide is dosed in 28 kg of purified water, and complete dissolution is ascertained (solution 1);
2. 1530 g of boric acid is dosed, dissolved in 71 kg of purified water at 40–45° C., and complete dissolution is ascertained (solution 2);
3. solution 1 is joined to solution 2; 394.07 kg of purified water is added and the mixture is stirred for 15 minutes;
4. to the solution thus obtained 500 kg of isopropanol is added slowly, while stirring;
5. 5 kg of chloramine-T is added, and the mixture is stirred for 30 minutes, and finally filtered with a 1 μm filter.

The product thus obtained may be stored at room temperature for at least eighteen months without undergoing any appreciable loss of active chlorine. In the event that a commercial product with shelf life of several years is desired, the bottle may be packaged with a suitable dosing cap, wherein the prescribed amount of chloramine is kept separate from the hydroalcoholic solution. Just before opening the bottle, by acting on the dosing cap the two components are contacted with each other and mixed, ad the final desired formulation is obtained. The product thus obtained may be kept in the mixed state for at least eighteen months.

Stability tests

With the preparation obtained according to the above procedure, having the following composition (percentage by weight):

| | |
|---|---|
| chloramine-T | 0.5% |
| | (1120 ppm of active chlorine) |
| isopropanol | 50% |
| boric acid | 0.153% |
| sodium hydroxide | 0.0396% |
| purified water | q.s. to 100% | and having a pH of 10.4–10.9, stability tests at room temperature were carried out, in order to ascertain the possibility of storing the product with no appreciable alterations for at least eighteen months. The results of such tests for two different batches of product are set forth in the following table.

TABLE 2

Long term stability at room temperature

| | Batch A | | | | Batch B | | |
|---|---|---|---|---|---|---|---|
| Time | active chlorine | | alcohol | | active chlorine | | alcohol |
| (months) | (ppm) | (%) | (%) | pH | (ppm) | (%) | (%) | pH |
| 0 | 1120 | 100.0 | 49.9 | 10.76 | 1120 | 100.0 | 50.2 | 10.88 |
| 1 | 1113 | 99.4 | 50.0 | 10.81 | 1120 | 97.5 | 50.2 | 10.79 |
| 4 | 1085 | 96.9 | 50.1 | 10.69 | 1092 | 97.5 | 50.3 | 10.81 |
| 5 | 1085 | 96.9 | 50.1 | 10.83 | 1092 | 97.5 | 50.2 | 10.75 |
| 6 | 1085 | 96.9 | 50.2 | 10.71 | 1092 | 97.5 | 50.4 | 10.69 |
| 9 | 1042 | 93.0 | 50.7 | 10.80 | 1064 | 95.0 | 50.6 | 10.77 |
| 12 | 1028 | 91.8 | 50.5 | 10.71 | 1021 | 91.2 | 50.5 | 10.53 |
| 15 | 1035 | 92.4 | 50.2 | 10.79 | 1014 | 90.5 | 50.3 | 10.62 |
| 18 | 1021 | 91.2 | 50.2 | 10.68 | 993 | 88.7 | 50.3 | 10.44 |

It is clear from the preceding data that the preparation according to the invention has an optimal stability in spite of the coexistence of the chlorine-based compound with alcohol. The concentration of active chlorine is not remarkably reduced even after several months of storage.

In order to ascertain the stability of the formulation according to the invention in the same experimental conditions as described in the in the patent document DD 2255, referred to in the foregoing in connection with the prior art, the amount of active chlorine present in the preparation according to the invention after exposure at a temperature of 50° C. for several hours was measured, obtaining the results shown in the following table.

TABLE 3

Stability vs time at 5000

| Time | % active chlorine |
|---|---|
| 16 hours | 99.4 |
| 48 hours | 98.7 |
| 1 week | 96.3 |

In view of the fact that the cited prior art document reports (and considers as satisfactory) an amount of active chlorine of 95.5% after 16 hours (4.5% loss), the advantage brought by the formulation according to the invention is readily apparent.

Activity tests

1. Intrinsic bactericidal activity—1$^{st}$ series of tests

In order to ascertain the activity of the antiseptic product of the invention, the same preparation of the Example underwent a series of in vitro tests at various concentrations, employing as the test microorganisms a strain of *Staphylococcus aureus*, i.e. the ATCC 6538 strain, and a strain of *Pseudomonas aeruginosa*, i.e. the ATCC 15442 strain. Both strains were supplied by the American Type Culture Collection (Maryland, USA).

Before use the bacterial strains, that had been kept frozen, were transplanted on slants of Tryptone Soya Agar (TSA, Merck) and were kept in refrigerator at 4° C.±1° C. At the time of preparation, the bacterial strains were transplanted three times on TSA slants and incubated at 37° C.±2° C. for 18 hours; two hours before the test the final culture was suspended in diluent using 5 g of glass beads, and the suspension was diluted to obtain a count of about $1.5$–$5·10^8$ colony-forming units per ml of suspension (cfu/ml). The diluent employed contained 1.0 g of meat peptone and 8.5 g of NaCl in q.s. to 1000 ml of distilled water. In order to count the bacterial suspensions under test, $10^{-6}$ and $10^{-7}$ dilutions in the cited diluent were prepared, and from any one of said dilutions two aliquots of 1 ml each were taken, and were transferred on Petri dishes, in 15 ml of TSA. After incubation of the dishes for 24 hours at 37° C.±2° C. the colonies were counted, and the number of colony-forming units per ml was calculated according to the following formula: cfu/ml=$C/(n·V·d)$, wherein C is the sum of the colonies counted on both dishes, n=2 is the number of the dishes, V is the volume of the bacterial suspension placed on each dish and d is the dilution factor corresponding to the dilution realized. The value thus obtained, referred to as N, represents the bacterial count of the starting suspension.

The bactericidal activity tests, carried out in accordance with the standard CEN/TC 216 PrEN 1040 of September 1996, consisted in placing the bacterial cultures prepared as above into contact with the product under test, at 20° C.±2° C. and for a period of time of 5 minutes, and in detecting the reduction of the viability of the cultures resulting from the action of the product. On the basis of preliminary tests 0.5 wt % sodium tiosulfate was chosen as the neutralizing agent (to inactivate the action of the disinfectant after the fixed contact time). The product according to the invention has been proved at various weight concentrations, resulting from the dilution with distilled water. The concentration of the starting product was 1.25 times the effective test concentration.

In each assay the sample under test (at the initial concentration), the bacterial suspensions and the neutralizing agent were previously stabilized at 20° C.±2° C., and 8 ml of each sample under test was transferred in a sterile test tube, where 1 ml of bacterial suspension was added, prepared as above. After the fixed contact time (5 min.) the product was inactivated by transferring 1 ml thereof in a test tube containing 8 ml of neutralizing agent and 1 ml of distilled water, and thoroughly stirring the mixture. After the neutralization period (5 min.±10 sec.) the number of surviving microorganisms in the mixture was determined in double. The count was made by inclusion in agar, incubating the dishes for 24 hours at 37° C.±2° C. and counting the colony-forming units in the same way as described above for the count of the value of cfu/ml in the starting bacterial suspensions. The numerical value thus obtained, referred to as $N_a$, represents the bacterial count in a suspension exposed for 5 min. to the product under test, the test being applied, however, on a bacterial suspension 10 times more diluted than the starting solution. Therefore, the calculation of the reduction of bacterial viability resulting from the contact with the product under test may be made by applying the following formula: viability reduction=$N \cdot 10^{-1}/N_a$.

The following Table 4 reports the results of the tests carried out as as above for two different effective product concentrations (corresponding to 80% and to 50% by weight, respectively) both in terms of bacterial count (values of N and $N_a$) and in terms of reduction of the bacterial viability. In counting the colony-forming units the value>$3.0 \cdot 10^3$ has been conventionally assigned when the number of colony-forming units was more than 300 in both dishes. On the basis of the above-mentioned standard, the product is considered to show a bactericidal activity if, in the test conditions, the bacterial viability detected is reduced by at least a factor of $10^5$.

Staphylococcus aureus ATCC 33501
Clostridium difficile ATCC 17858
Streptococcus pyogenes ATCC 8058

Before use the bacterial suspensions, after repeated passages, were diluted to obtain a bacterial count of about $1.0$–$3.9 \cdot 10^8$ colony-forming units per ml of suspension (cfu/ml), as shown in the following table. Each bacterial strain was contacted with the product under test and with the 10% serum albumin in the following proportions: 8:1:1, respectively, for disinfectant preparation, bacterial suspension and serum albumin. The strains were incubated at 24° C. for time intervals of 15 sec., 30 sec. and 60 sec., and immediately after the end of the incubation period the product was inactivated by diluting it in the ratio 1:1000 (v/v) with phosphate buffered saline (PBS), pH 7.2. After the inactivation, an inoculum from each suspension was cultured for 18–24 hours in the following culture media: *E. coli, P. aeruginosa, S. marcescens, K. pneumoniae, S. dissenteriae, P. vulgaris:* Nutrient agar; *S. aureus. S. epidermidis:* Trypticase soy agar (Trypticase soy broth (BBL 11768) 30.0 g, agar 15.0 g, distilled water 1.0 l); *S. pyogenes:* Rabbit blood agar; *C. difficile:* Beef liver medium for anaerobes (ATCC culture medium 38). The temperature conditions were as follows: *E. coli, K. pneumoniae, S. dissenteriae, P. vulgaris, S. aureus, S. epidermidis, C. difficile* (+anaerobiosis), *S. pyogenes.* 37° C.; *P. aeruginosa, S. marcescens:* 26° C.

At the end of the culture period the colonies formed were counted, and the number of colony-forming units per ml (cfu/ml) was calculated according to the same formula given in the previous section. The controls employed in the test

TABLE 4

| | Base bactericidal activity | | | | |
|---|---|---|---|---|---|
| | | Conc. 80% | | Conc. 50% | |
| | N (cfu/ml) | $N_a$ (cfu/ml) | Viability reduct. | $N_a$ (cfu/ml) | Viability reduct. |
| Staphylococcus aureus ATCC 6538 | $1.7 \cdot 10^8$ | $1.4 \cdot 10^2$ | $1.2 \cdot 10^5$ | >$3.0 \cdot 10^3$ | <$5.7 \cdot 10^3$ |
| Pseudomonas aeruginosa ATCC 15442 | $1.6 \cdot 10^8$ | $1.5 \cdot 10^2$ | $1.1 \cdot 10^5$ | >$3.0 \cdot 10^3$ | <$5.7 \cdot 10^3$ |

As it can be observed from the preceding data, the product according to the invention appears to possess an intrinsic bactericidal activity at a dilution of 80% by weight with respect to the formulation as produced in the Example.

1. Intrinsic bactericidal activity—2$^{nd}$ series of tests

A second series of in vitro tests were carded out employing the same preparation of the Example, with a wider set of microorganisms and conditions more similar to those actually occurring in the normal use of a disinfectant, i.e., in the presence of a high concentration of organic matter. The organic matter employed was bovine serum albumin, in amounts such as to obtain a final concentration of 10% by weight in each test sample. The strains employed, all supplied by the American Type Culture Collection (Maryland, USA), are listed below:

Escherichia coli ATCC 4351
Pseudomonas aeruginosa ATCC 12121
Serratia marcescens ATCC 8101
Klebsiella pneumoniae ATCC 4211
Shigella dissenteriae ATCC 9380
Proteus vulgaris ATCC 6361
Staphylococcus epidermidis ATCC 35696 were the same bacterial suspensions, treated with PBS (pH 7.2) instead of the disinfectant under test, in the same conditions and for the same times. The following Table 5 reports the results of the tests carried out as described above.

TABLE 5

| | Base bactericidal activity | | | |
|---|---|---|---|---|
| | inoculum (cfu/ml) | 15 sec. (cfu/ml) | 30 sec. (cfu/ml). | 60 sec. (cfu/ml) |
| C. difficile | $1.0 \cdot 10^8$ | <100 | <100 | <100 |
| E. coli | $1.6 \cdot 10^8$ | <100 | <100 | <100 |
| S. pyogenes | $2.2 \cdot 10^8$ | <100 | <100 | <100 |
| P. aeruginosa | $3.9 \cdot 10^8$ | $0.32 \cdot 10^3$ | <100 | <100 |
| S. marcescens | $2.4 \cdot 10^8$ | $0.68 \cdot 10^3$ | <100 | <100 |
| K. pneumoniae | $1.1 \cdot 10^8$ | $0.23 \cdot 10^3$ | <100 | <100 |
| S. dissenteriae | $1.7 \cdot 10^8$ | <100 | <100 | <100 |
| P. vulgaris | $1.2 \cdot 10^8$ | <100 | <100 | <100 |
| S. epidermidis | $2.0 \cdot 10^8$ | $1.4 \cdot 10^2$ | <100 | <100 |
| S. aureus | $1.0 \cdot 10^8$ | $0.22 \cdot 10^3$ | <100 | <100 |

The results reported in the above table show a virtually complete inhibition (values below 100 cfu/ml) after 30 seconds of incubation for all of the bacterial strains tested. Even after 15 seconds of contact between the microorganisms and the product of the invention the bacterial counts obtained are, for the totality of the strains tested, equivalent to a reduction by a factor of at least $10^5$, this being the limit, as pointed out in the previous section, for establishing an antimicrobial activity.

2. Bactericidal activity in the conditions of use for the hands

Tests similar to those reported as the $1^{st}$ series of tests for intrinsic bactericidal activity were carried out according to the standard CEN prEN 12054 of July 1995, relevant to the hands treatment before surgery (i.e. surgical handrub). The strains *Pseudomonas aeruginosa* ATCC 15442, *Staphylococcus aureus* ATCC 6538, *Enterococcus faecium* ATCC 10541 and *Escherichia coil* K12 NCTC 10538 were used, all of them supplied by the American Type Culture Collection (Maryland, USA).

The preparation of the starting bacterial suspensions and the calculation of the number of colony-forming units (N) of said bacterial suspensions were the same as in the previous test, with the only difference that the bacterial count in the initial suspensions was about $1-3 \cdot 10^8$ cfu/ml. Also the choice of the neutralizing agent and the temperature of performance of the test (20° C.±2° C.) were the same as in the previous test, but the effective concentration of product used was of 90% by weight, and the measures were taken for two different contact times, i.e. 2 minutes and 5 minutes.

For each bacterial strain a test tube was prepared containing 9 ml of product under test and 1 ml of bacterial suspension, and at the end of each contact time 1 ml of the mixture was transferred in a test tube containing 8 ml of neutralizing agent and 1 ml of distilled water. After 5 minutes of neutralization the mixture was vortexed and the count was carried out, in double, with the same procedure as the previous test, obtaining the values of cfu/ml after exposure to the product ($N_a$) for the fixed periods of time. In the cfu count, the value<$3,0 \cdot 10^2$ has been conventionally assigned when the number of colony-forming units was lower than 300 in both dishes. In this case the material under test is considered to be bactericidal when it causes, for each strain, a reduction of the bacterial count from $1-3 \cdot 10^8$ cfu/ml to no more than $3 \cdot 10^2$ cfu/ml after 5 minutes of contact.

TABLE 6

Bactericidal activity in the conditions of use on the hands

| | | 90% Concentration | | | |
|---|---|---|---|---|---|
| | | after 3 min. | | after 5 min. | |
| | N (cfu/ml) | colony count | $N_a$ (cfu/ml) | colony count | $N_a$ (cfu/ml) |
| *Staphylococcus aureus* ATCC 6538 | $1.49 \cdot 10^8$ | 29-27 | $2.8 \cdot 10^2$ | 18-13 | $1.55 \cdot 10^2$ |
| *Pseudomonas aeruginosa* ATCC 15442 | $1.65 \cdot 10^8$ | 30-36 | $2.8 \cdot 10^2$ | 14-19 | $1.6 \cdot 10^2$ |
| *Escherichia coli* K12 NCTC 10538 | $1.80 \cdot 10^8$ | 0-0 | $<3.0 \cdot 10^2$ | 0-0 | $<3.0 \cdot 10^2$ |
| *Enterococcus faecium* ATCC 10541 | $1.99 \cdot 10^8$ | 14-21 | $1.71 \cdot 10^2$ | 0-0 | $<3.0 \cdot 10^2$ |

As it is noted from the data in the above table, the product according to the invention appears to possess the desired bactericidal activity also after a time of exposure of 3 minutes only.

3. Practical test for bactericidal activity on the hands—comparison with 60% isopropanol By using a strain of *Escherichia coil* K1-2 - NCTG 105~38 obtained from the Sierotherapic Center of Milan, Italy, some tests were carried out to ascertain the antiseptic and hygienizing activity of the product of the Example in the normal use conditions for hands washing. For the test 12 volunteers of both sexes were employed, selected on the basis of the perfectly intact status of the skin, the good general health conditions and the absence of ongoing pathologies and pharmacological treatments.

*Escherichia coli* was cultured in two test tubes containing 5 ml of TSB (Tryptone Soya Broth, Merck) for 24 hours at 37° C.±2° C. and the cultures were inoculated in two bottles containing 1 l of TSB each, and incubated for 24 hours at 37° C.±2° C. This contaminating liquid contains about $2 \cdot 10^8 - 2 \cdot 10^9$ cfu/ml, the number of colonies having been determined by carrying out the count in double by inclusion in agar, incubating the Petri dishes at 37° C.±1° C. for 24 hours.

At the beginning of the test, all of the voluntaries washed their hands with a linseed oil soap to remove the dirt naturally present, and then dried their hands with disposable paper towels. Each voluntary dipped then his fingertips in the bacterial suspension for 5 seconds, and dried them in air for 3 minutes. Immediately after, each voluntary dipped for 1 minute his contaminated fingertips of both hands respectively in two Petri dishes containing 10 ml of TSB, so as to allow the evaluation of the number of microorganisms released before the treatment. From the fluid thus obtained decimal dilutions $10^{-3} - 10^{-4}$ were prepared, and for each dilution 0.1 ml were spread on the surface of Petri dishes containing TSA, by using glass beads. The dishes were then incubated at 37° C.±2° C. for 24 hours, and the number of colonies for each dilution was counted, calculating the arithmetic mean thereof. The number of colonies counted was then transformed in the decimal logarithmic value, and is referred to as Log x (basal contamination values).

Immediately after the determination of the initial values, and without recontamination of the hands, 6 of the 12 volunteers were treated with a comparative solution of isopropyl alcohol 60% v/v and the other 6 were treated with the solution according to the invention. The first 6 volunteers washed both hands with 3 ml of isopropyl alcohol for 30 seconds and then repeated the operation with other 3 ml of alcohol for 60 seconds. They finally rinsed their hands for 5 seconds with running water. The other 6 volunteers used a surgical gauze soaked with 4 ml of the product under test, cleaning their hands for 1 minute, and left then dry their hands in the air for 2 minutes.

The volunteers of both groups dipped then for 1 minute their fingertip of both hands in two Petri dishes respectively, and the same procedure reported above was repeated for the determination of the number of bacterial colonies originated. The values of the decimal logarithms thus obtained are indicated as Log y (post-treatment values). The logarithmic values of the reduction of the bacterial count from the basal value to the post-treatment value are referred to as Log 2.

In a second stage of the test the whole procedure was repeated with the same volunteers, after having exchanged the two products under test. Therefore, for each subject the following Table 7 shows either the values relevant to the treatment with isopropanol and the values relevant to the treatment with the preparation of the invention.

TABLE 7

Practical test of bactericidal activity on the hands

| Voluntary | 60% isopropanol | | | Product of the invention | | |
|---|---|---|---|---|---|---|
| No. | Log x | Log y | Log z | Log x | Log y | Log z |
| 1 | 6.49 | 4.11 | 2.37 | 6.37 | 1.75 | 4.62 |
| 2 | 6.41 | 4.20 | 2.21 | 6.32 | 1.92 | 4.40 |
| 3 | 6.33 | 4.35 | 1.98 | 6.30 | 1.83 | 4.47 |
| 4 | 6.38 | 3.78 | 2.60 | 6.33 | 1.45 | 4.88 |
| 5 | 6.36 | 3.87 | 2.49 | 6.48 | 1.91 | 4.57 |
| 6 | 6.42 | 4.07 | 2.35 | 6.43 | 1.82 | 4.61 |
| 7 | 6.44 | 4.27 | 2.17 | 6.36 | 1.80 | 4.56 |
| 8 | 6.38 | 4.38 | 2.00 | 6.41 | 1.88 | 4.53 |
| 9 | 6.26 | 4.28 | 1.98 | 6.32 | 1.86 | 4.46 |
| 10 | 6.24 | 4.00 | 2.64 | 6.32 | 1.67 | 4.65 |
| 11 | 6.22 | 4.49 | 2.73 | 6.20 | 1.52 | 4.68 |
| 12 | 6.37 | 3.46 | 2.91 | 6.35 | 1.91 | 4.44 |

It is evident from the above results that the formulation of chloramine-T in 50% isopropanol solution according to the invention has an antiseptic activity remarkably higher than that of the comparison disinfectant product, i.e. 60% isopropanol.

Cutaneous irritation tests

In order to ascertain the cutaneous tolerability of the product of the Example, a test on 3 male New Zealand albino rabbits was carried out. The rabbits, weighing 2.5–3.5 kg, had been randomly selected among a certain number of animals that had been previously kept in quarantine for a week and then underwent, before the test, a thorough examination to ascertain their suitability for the test. The back and the sides of the animals were shaved 24 hours before starting the test, on an area of about 240 $cm^2$, and an area of about 20 $cm^2$ on the right side has been used for applying the sample under test, while the left side, untreated, served as a control. 0.5 ml of the product were applied by means of a square piece of surgical gauze directly on the skin, and the gauze was fixed with a plaster. The square gauze was further fixed with an occlusive hypoallergenic adhesive tape, and the whole trunk of the animal was protected by an elastic medication.

About 4 hours after the application, the medications and the adhesives were removed, and the skin was cleaned from the excess sample. The cutaneous reactions of the animals were evaluated one hour after the removal of the gauze. For the evaluation of the cutaneous reactions the following score scales were used:

Erythema and eschar formation: 0=absence of erythema; 1=light erythema (hardly visible); 2=well-visible erythema; 3=erythema from moderate to severe; 4=severe erythema (beet red) or eschar formation (deep lesions). Oedema formation: 0=absence of oedema; 1=very light oedema (hardly visible); 2=light oedema (margins of the inflated zone well defined); 3=moderate oedema (margins projecting by about 1 mm); 4=strong oedema (margins projecting by more than 1 mm, inflation extended beyond the area of application).

The values of the cutaneous reactions found in each of the three rabbits after 60 minutes, 24 hours, 48 hours and 72 hours from the removal of the gauze with the product under test, evaluated by means of the above score scales, have always been equal to 0, indicating the total absence of any erythematous and/or oedematous reaction.

The present invention has been disclosed with particular reference to some specific embodiments thereof, but it should be understood that modifications and changes may be made by the persons skilled in the art without departing from the scope of the invention as defined in the appended claims.

What is claimed is:

1. A disinfecting preparation containing chlorine in an alcohol solution comprising, in water, chloramine-T or chloramine-B at a concentration corresponding to 1000–2500 ppm of available chlorine and one or more aliphatic alcohols having up to 12 carbon atoms, said solution having a pH not lower than 8.5.

2. The disinfecting preparation according to claim 1 comprising, in addition, a buffer suitable to maintain the pH at a value not below 8.5.

3. The disinfecting preparation according to claim 1, wherein the aliphatic alcohol or alcohols are chosen from ethanol, n-propanol and isopropanol.

4. The disinfecting preparation according to claim 3, wherein said ethanol, n-propanol and/or isopropanol are present in an overall concentration of 40 and 70% by weight.

5. The disinfecting preparation according to claim 2, wherein said buffer is borate buffer.

6. The disinfecting preparation according to claim 5, having the formulation:

| | |
|---|---|
| chloramine-T or chloramine-B | 1000–2500 ppm of available chlorine |
| ethanol or isopropanol | 50–60% by weight |
| pH | >8.5 |
| boric acid | 0.153–0.155% by weight |
| sodium hydroxide | 0.0396–0.064% by weight |
| water | q.s. to 100%. |

7. The disinfecting preparation according to claim 6, wherein chloramine-T is present.

8. The disinfecting preparation according to claim 6, wherein isopropanol is present.

9. The disinfecting preparation according to claim 8, wherein the concentration of isopropanol is 50 % by weight.

10. The disinfecting preparation according to claim 6, wherein the pH is between 10.4 and 10.9.

* * * * *